(12) United States Patent
Ramachandran et al.

(10) Patent No.: US 10,179,354 B2
(45) Date of Patent: Jan. 15, 2019

(54) OPTICAL ENDPOINT DETECTION SYSTEM

(71) Applicant: APPLIED MATERIALS, INC., Santa Clara, CA (US)

(72) Inventors: Balasubramanian Ramachandran, Santa Clara, CA (US); Masato Ishii, Sunnyvale, CA (US); Aaron Muir Hunter, Santa Cruz, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 178 days.

(21) Appl. No.: 15/162,160

(22) Filed: May 23, 2016

(65) Prior Publication Data

US 2016/0263634 A1    Sep. 15, 2016

Related U.S. Application Data

(62) Division of application No. 13/440,564, filed on Apr. 5, 2012, now Pat. No. 9,347,132.

(Continued)

(51) Int. Cl.
| | |
|---|---|
| *B08B 9/46* | (2006.01) |
| *H01L 21/67* | (2006.01) |
| *C23C 16/44* | (2006.01) |
| *C23C 16/52* | (2006.01) |
| *B08B 3/08* | (2006.01) |

(Continued)

(52) U.S. Cl.
CPC .......... *B08B 9/46* (2013.01); *B08B 3/08* (2013.01); *B08B 3/10* (2013.01); *C23C 16/4405* (2013.01); *C23C 16/52* (2013.01); *G01N 21/94* (2013.01); *H01L 21/67253* (2013.01); *G01N 2021/8416* (2013.01)

(58) Field of Classification Search
None
See application file for complete search history.

(56) References Cited

U.S. PATENT DOCUMENTS

| | | |
|---|---|---|
| 6,737,666 B1 | 5/2004 | Ito et al. |
| 2004/0011379 A1 | 1/2004 | Anaokar et al. |

(Continued)

FOREIGN PATENT DOCUMENTS

| | | | | |
|---|---|---|---|---|
| CN | 101010446 A | * | 8/2007 | ........... B08B 7/0035 |
| JP | 11-140655 A | | 5/1999 | |

(Continued)

OTHER PUBLICATIONS

Machine translation of JP 11140655, retrieved Aug. 2015.*

(Continued)

*Primary Examiner* — Eric W Golightly
(74) *Attorney, Agent, or Firm* — Moser Taboada; Alan Taboada

(57) ABSTRACT

Methods and apparatus for determining an endpoint of a process chamber cleaning process are provided. In some embodiments, a method of monitoring a process being performed in a process chamber includes: performing a cleaning process in a process chamber to remove material deposited on one or more internal surfaces of the process chamber resultant from processes performed within the process chamber; shining a light on a first internal surface being cleaned; detecting the light reflected off of the first internal surface; and terminating the cleaning process based upon the detected light.

13 Claims, 3 Drawing Sheets

Related U.S. Application Data

(60) Provisional application No. 61/480,839, filed on Apr. 29, 2011.

(51) Int. Cl.
*B08B 3/10* (2006.01)
*G01N 21/94* (2006.01)
*G01N 21/84* (2006.01)

(56) References Cited

U.S. PATENT DOCUMENTS

| | | |
|---|---|---|
| 2006/0021633 A1 | 2/2006 | Harvey |
| 2006/0228473 A1 | 10/2006 | Satoh et al. |
| 2008/0261335 A1 | 10/2008 | Grimbergen |

FOREIGN PATENT DOCUMENTS

| | | | |
|---|---|---|---|
| JP | 2002-246320 A | | 8/2002 |
| JP | 3138693 U | | 1/2008 |
| KR | 10-2004-0055344 A | | 6/2004 |
| TW | 200844667 | * | 11/2008 |

OTHER PUBLICATIONS

International Search Report and Written Opinion dated Nov. 28, 2012 for PCT Application No. PCT/US2012/035469.
Search Report received from the State Intellectual Property Office of The People's Republic of China dated Sep. 6, 2015 for Chinese Application No. 2012800199705.
Search Report for Taiwan Invention Patent Application No. 101114953 dated Oct. 15, 2015.

* cited by examiner

OPTICAL ENDPOINT DETECTION SYSTEM

CROSS-REFERENCE TO RELATED APPLICATIONS

This application is a divisional of co-pending U.S. patent application Ser. No. 13/440,564, filed Apr. 5, 2012, and issued as U.S. Pat. No. 9,347,132 on May 24, 2016, which claims benefit of U.S. provisional patent application Ser. No. 61/480,839, filed Apr. 29, 2011. Each of the aforementioned related patent applications is herein incorporated by reference.

FIELD

Embodiments of the present invention generally relate to substrate processing apparatus.

BACKGROUND

Typical processing in substrate process chambers causes various deposits to form on the process chamber walls. These deposits are generally removed by a cleaning process run in the chamber without a substrate present. One such cleaning process, used for example in epitaxial deposition systems, involves hydrogen chloride (HCl) and high temperature.

The cleaning process must be performed for a sufficient time to ensure that the internal process chamber surfaces and components are clean. In some instances, the cleaning process may be performed for too long of a period, which not only removes the unwanted deposits, but also may cause a significant amount of degradation of chamber surfaces and components. On the other hand, if the cleaning process is performed for too short of a period, a significant amount of deposits may remain on the process chamber surfaces, resulting in an increase in process drift and/or defects (e.g., particles). Thus, a balance is generally established between tolerating process drift and increased defects and the need to increase the lifetime of chamber components.

One method for finding the balancing point is to perform visual observations after an extended period of time. However, this is generally a subjective process and is prone to errors. Another method for finding the balancing point is to rely on process/defect trends (as substrates are being processed). However, this is tedious and causes unnecessary usage of substrates and resources.

Thus, the inventors have provided improved methods and apparatus for determining the endpoint of chamber cleaning processes.

SUMMARY

Methods and apparatus for determining an endpoint of a process chamber cleaning process are provided. In some embodiments, a processing system having an endpoint detection system may include a process chamber having internal surfaces requiring periodic cleaning due to processes performed in the process chamber; and an endpoint detection system that includes a light detector positioned to detect light reflected off of a first internal surface of the process chamber; and a controller coupled to the light detector and configured to determine an endpoint of a cleaning process based upon the detected reflected light.

In some embodiments, a method of monitoring a cleaning process being performed in a process chamber may include performing a cleaning process in a process chamber to remove material deposited on one or more internal surfaces of the process chamber resultant from processes performed within the process chamber; shining a light on a first internal surface being cleaned; detecting the light reflected off of the first internal surface; and terminating the cleaning process based upon the detected light.

In some embodiments, a computer readable medium may be provided having instructions stored thereon that, when executed, cause a processing system to perform a method of monitoring a cleaning process being performed in a process chamber. The method may include any of the embodiments disclosed herein.

Other and further embodiments of the present invention are described below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

Figure 1:
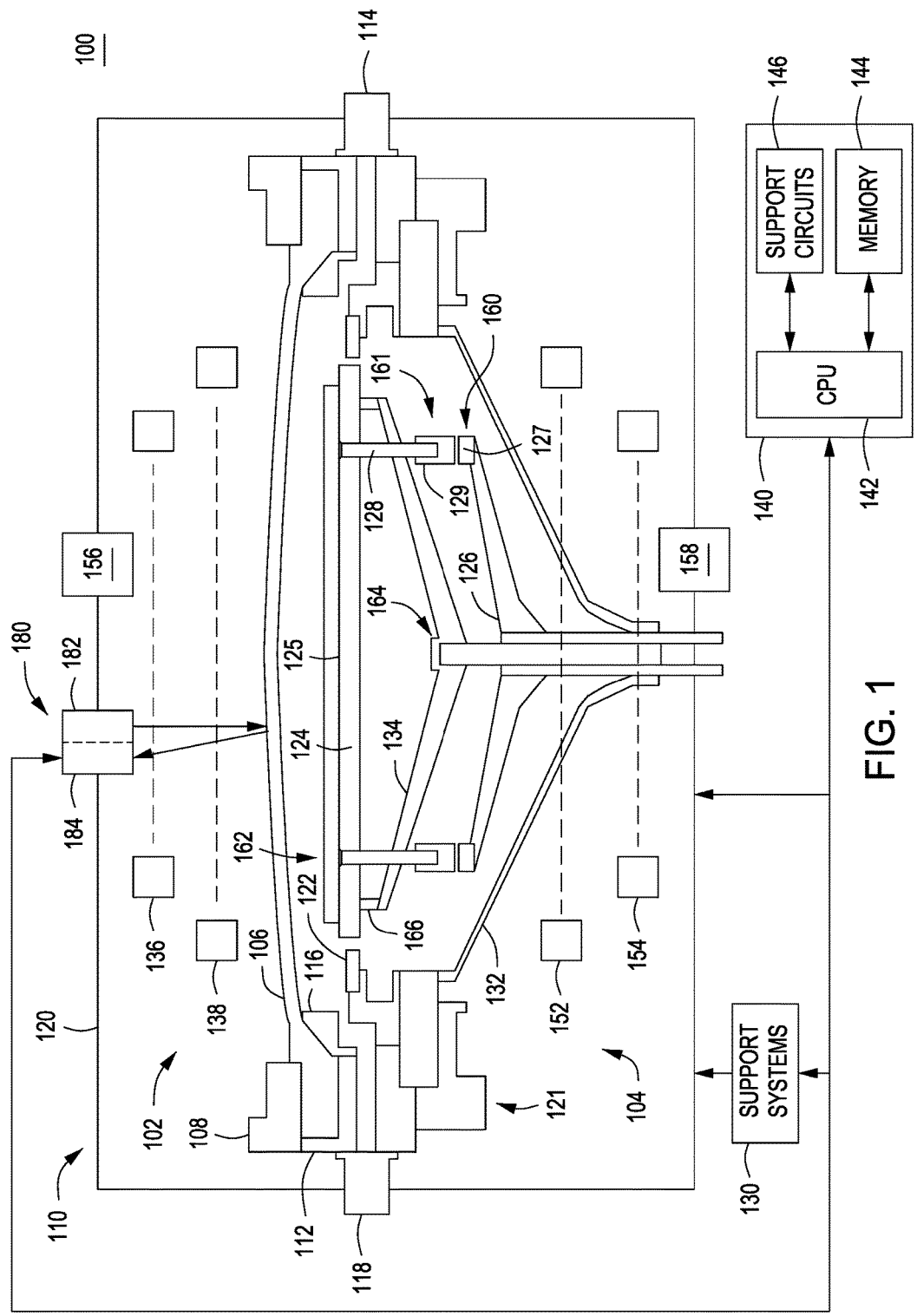
FIG. 1 depicts a schematic, cross-sectional view of a semiconductor substrate process chamber in accordance with one embodiment of the present invention.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments of the present invention relate to methods and apparatus for determining an endpoint of a process chamber cleaning process. Embodiments of the methods and apparatus may advantageously provide an accurate endpoint detection for a cleaning process such that wear on process chamber components from the cleaning process may be minimized while minimizing process drift and defects due to insufficient process chamber cleaning.

Various process chambers may benefit from modification in accordance with the teachings provided herein. FIG. 1 is a schematic, cross-sectional view of a semiconductor substrate process chamber 100 in accordance with some embodiments of the present invention and suitable for performing the inventive methods disclosed herein. In the depicted embodiment, the process chamber 100 is adapted for performing epitaxial silicon deposition processes. One such suitable reactor is the RP Epi reactor, available from Applied Materials, Inc. of Santa Clara, Calif. The methods of the present invention may also be utilized in other process chambers for performing other processes.

In alternate embodiments, the process chamber 100 may be adapted for performing at least one of deposition processes, etch processes, plasma enhanced deposition and/or etch processes, and thermal processes, among other processes performed in the manufacture of integrated semiconductor devices and circuits. Specifically, such processes may include, but are not limited to, rapid thermal processes (RTPs), chemical vapor deposition (CVD) processes, annealing processes, and the like.

The process chamber 100 illustratively comprises a chamber body 110, support systems 130, and a controller 140. The chamber body 110 generally includes an upper portion 102, a lower portion 104, and an enclosure 120.

The upper portion 102 is disposed on the lower portion 104 and includes a lid 106, a clamp ring 108, a liner 116, a baseplate 112, one or more upper lamps 136 and one or more lower lamps 138, and an upper pyrometer 156. In some embodiments, the lid 106 has a dome-like form factor, however, lids having other form factors (e.g., flat or reverse-curve lids) are also contemplated. The lower portion 104 is coupled to a process gas intake port 114 and an exhaust port 118 and comprises a baseplate assembly 121, a lower dome 132, a substrate support 124, a pre-heat ring 122, a substrate lift assembly 160, a substrate support assembly 164, one or more upper lamps 152 and one or more lower lamps 154, and a lower pyrometer 158. Although the term "ring" is used to describe certain components of the process chamber, such as the pre-heat ring 122, it is contemplated that the shape of these components need not be circular and may include any shape, including but not limited to, rectangles, polygons, ovals, and the like.

The substrate support assembly 164 generally includes a support bracket 134 having a plurality of support pins 166 coupled to the substrate support 124. The substrate lift assembly 160 comprises a substrate lift shaft 126 and a plurality of lift pin modules 161 selectively resting on respective pads 127 of the substrate lift shaft 126. In some embodiments, a lift pin module 161 comprises an optional base 129 and a lift pin 128 coupled to the base 129. Alternatively, a bottom portion of the lift pin 128 may rest directly on the pads 127. In addition, other mechanisms for raising and lowering the lift pins 128 may be utilized. An upper portion of the lift pin 128 is movably disposed through a first opening 162 in the substrate support 124. In operation, the substrate lift shaft 126 is moved to engage the lift pins 128. When engaged, the lift pins 128 may raise the substrate 125 above the substrate support 124 or lower the substrate 125 onto the substrate support 124.

The support systems 130 include components used to execute and monitor pre-determined processes (e.g., growing epitaxial silicon films) in the process chamber 100. Such components generally include various sub-systems (e.g., gas panel(s), gas distribution conduits, vacuum and exhaust sub-systems, and the like) and devices (e.g., power supplies, process control instruments, and the like) of the process chamber 100.

During processing, a substrate 125 is disposed on the substrate support 124. The lamps 136, 138, 152, and 154 are sources of infrared (IR) radiation (i.e., heat) and, in operation, generate a pre-determined temperature distribution across the substrate 125. In some embodiments, the lid 106, the clamp ring 116, and the lower dome 132 are formed from quartz; however, other IR-transparent and process compatible materials may also be used to form these components.

As a result of processing the substrate, materials may undesirably deposit on interior surfaces of the process chamber (such as the liner 116, the lid 106, and the like). Failure to remove the materials deposited on the interior process chamber surfaces may undesirably lead to process drift and/or defect formation on the substrate. As such, a cleaning process is periodically performed to remove at least some of the deposited materials from the interior surfaces of the process chamber. For example, in some embodiments, the process chamber may be cleaned by exposing the surfaces to be cleaned to a reactant that removes the deposited material from the surfaces. One such cleaning process, used for example in epitaxial deposition systems, includes exposing the surfaces to hydrochloric acid (HCl) while heating the surfaces to a high temperature.

To provide an accurate endpoint detection for the cleaning process, such that wear on process chamber components from the cleaning process may be minimized while minimizing process drift and defects due to insufficient process chamber cleaning, the process chamber 100 further comprises an endpoint detection system 180. The endpoint detection system 180 facilitates determining a desired endpoint of the cleaning process.

The endpoint detection system 180 generally includes a light source 182. The light source 182 may be any suitable source of light that provides a detectable reflection off of the desired process chamber surface. For example the light source 182 may be a laser, a light emitting diode (LED), a lamp, or ambient light. In some embodiments, the light source 182 may provide a single wavelength of light. In some embodiments, the light source 182 may provide a plurality of wavelengths of light. The plurality of wavelengths may be provided in one or more continuous bands, or in a plurality of discrete wavelengths. In some embodiments, the light source may provide light having a wavelength of about 405 or 450 nm (e.g., blue light), 532 nm (e.g., green light), 633, 650, or 670 nm (e.g., red light), or the like. In some embodiments, the light source may provide light having any one or more wavelengths up to about the silicon band gap (e.g., about 1.2 µm).

In the embodiment depicted in FIG. 1, the light source 182 is configured to shine light onto the dome 106. In some embodiments, the light source 182 is configured to shine light onto the dome 106 in a region where a relatively high percentage of the deposited materials are deposited, such that when observing that the observed region is clean, then the remaining portions of the process chamber surface is also likely clean. The light source may be positioned to shine light onto any desired portion of the process chamber, and not just the dome 106. For example, the light source may be positioned to shine light onto the liner 116, the lower dome 132, or any other process chamber surface that has material deposited thereon and that is to be cleaned so long as the deposited material and the underlying process chamber surface reflect light in a different manner.

In some embodiments, the endpoint detection system 180 may further include a light detector 184. The light detector may be a camera, a photodiode-based light detector, or the like. Optional components, such as optics, lenses, collimators, filters, or the like, may be provided in conjunction with either or both the light source and the light detector to guide the light to and/or from the process chamber surface.

In some embodiments, the light detector and the light source may be disposed in a common housing. In some embodiments, the light detector and the light source may be separate components individually positioned to provide and detect the light. The light source 182 and the light detector 184 may be generally positioned anywhere such that the light is provided to a desired portion of a process chamber surface to be monitored and such that the reflected light impinges on the light detector. For example, the light source and light detector may be placed near each other, as shown in FIG. 1, or further spaced apart, including positioned on opposing sides of the chamber to provide light at a shallow angle to the desired portion of the chamber surface (such as the lid 106). In some embodiments, a plurality of light sources and, optionally, light detectors can be provided in the endpoint detection system to measure the thickness of the coating of deposited material and the cleanliness of the process chamber surfaces at different locations of the process chamber.

For example, the epitaxial deposition process chamber described above includes a quartz lid 106 on which the undesired materials deposit. The deposited material generally causes the otherwise clear and transparent lid 106 to take on a brownish appearance. In some embodiments, a light having a specific wavelength (such as a green laser pointer—about 532 nm) may be shone onto the lid 106. This causes light to reflect off from the lid 106 and from the brownish coating under the lid 106. The combined light beams cause an interference pattern which can be detected either by a camera, a photodiode based detector, or by the human eye. When the lid 106 area is clean, no interference pattern forms because there is no brownish coating on the lid 106, and a single specular reflection is observed.

A controller 140 may be used to facilitate control of the chamber 310 as described above. For example, the controller 140 may be coupled to various process chamber components such as the process chamber, control systems 130, and the endpoint detection system 180. The controller 140 may be one of any form of a general purpose computer processor used in an industrial setting for controlling various chambers and sub-processors. The controller 140 comprises a central processing unit (CPU) 142, a memory 144, and support circuits 146 for the CPU 142 and coupled to the various components of the process chamber 100 to facilitate control of the cleaning endpoint detection process as described herein. In some embodiments, the controller 140 may further include a display to visually indicate the status of the process or to display the detected light so that an operator may visually determine the status of the cleaning process.

The memory 144 is coupled to the CPU 142. The memory 144, or computer-readable medium, may be one or more of readily available memory such as random access memory (RAM), read only memory (ROM), floppy disk, hard disk, or any other form of digital storage, local or remote. The support circuits 146 are coupled to the CPU 142 for supporting the processor in a conventional manner. These circuits include cache, power supplies, clock circuits, input/output circuitry and subsystems, and the like. In some embodiments, a software routine, when executed by the CPU 142, causes the reactor to perform processes of the present invention. The software routine may generally be stored in the memory 144. The software routine may also be stored and/or executed by a second CPU (not shown) that is remotely located from the hardware being controlled by the CPU 142.

In some embodiments, the software routine may be executed while the cleaning process is being performed in the process chamber. The software routine 304, when executed by the CPU 142, transforms the general purpose computer into a specific purpose computer (controller) 140 that controls the chamber operation such that the etching process is performed. Although the process of the present invention is discussed as being implemented as a software routine, some of the method steps that are disclosed therein may be performed in hardware as well as by the software controller. As such, embodiments of the invention may be implemented in software as executed upon a computer system, in hardware as an application specific integrated circuit or other type of hardware implementation, or a combination of software and hardware.

Figure 2:
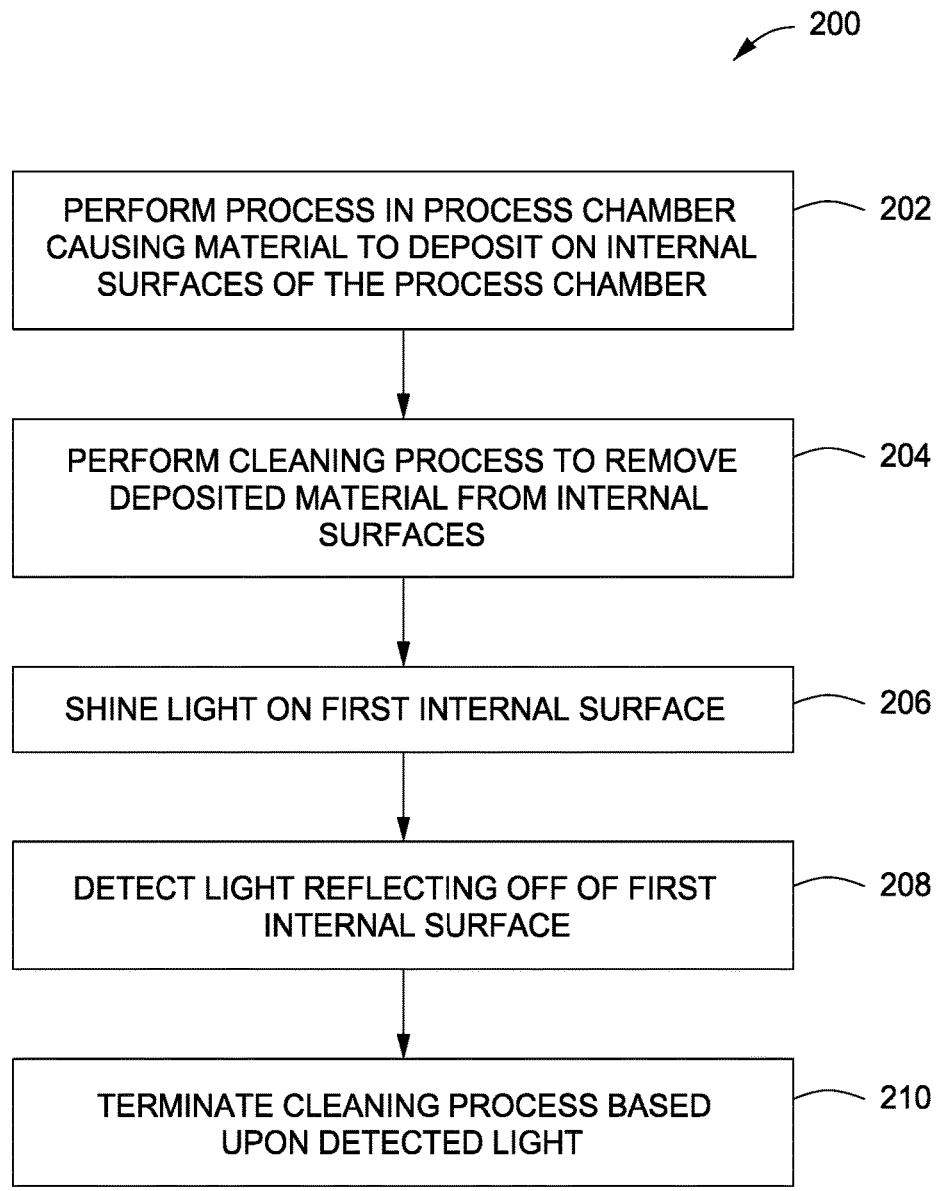
FIG. 2 depicts a method of monitoring a process being performed in a process chamber in accordance with some embodiments of the present invention.

FIG. 2 depicts a method 200 of monitoring a process being performed in a process chamber in accordance with some embodiments of the present invention. The method 200 generally begins at 202 where a process is performed in a process chamber causing material to deposit on internal surfaces of the process chamber. After sufficient material has deposited on the internal surfaces, or whenever a cleaning process is desired, the method may continue to 204, where a cleaning process may be performed to remove the deposited material from the process chamber internal surfaces.

While the cleaning process is being performed, a light may be shone on a first internal surface being cleaned by the cleaning process, as depicted at 206. The light may be provided by any of the light sources discussed above and may be provided continuously or periodically.

At 208, light reflected off of the first process chamber surface may be detected. The reflected light may be detected based upon a pattern, light intensity, or the like, and may be detected by eye, for example, by an operator of the process chamber, or via a detector as discussed above.

At 210, the cleaning process may be terminated based upon the detected light. For example, if the detected light shows an interference pattern, the cleaning process may continue as deposited material remains on the first process chamber surface. However, if the detected light shows no interference pattern (e.g., if a singular specular reflection is observed), then the cleaning process may be terminated as the deposited material is predominantly removed from the first process chamber surface.

In some embodiments, a plurality of different singular wavelengths of light may be provided and the interference patterns may further be analyzed to determine a thickness of the coating. For example, the size of the circular ring (e.g., interference pattern) can be used to determine thickness differences. Multiple wavelengths may be used to triangulate to a specific thickness solution. In some embodiments, a photo-diode based detector may be used to determine reflections that are specific to particular deposited materials. For example, silicon deposits (with a band gap of 1.1 eV) can be differentiated from germanium deposits (with a band gap of 0.67 eV) by using specific wavelengths to differentiate between the two. Other materials having dissimilar band gaps may also be similarly identified.

Figure 3A:
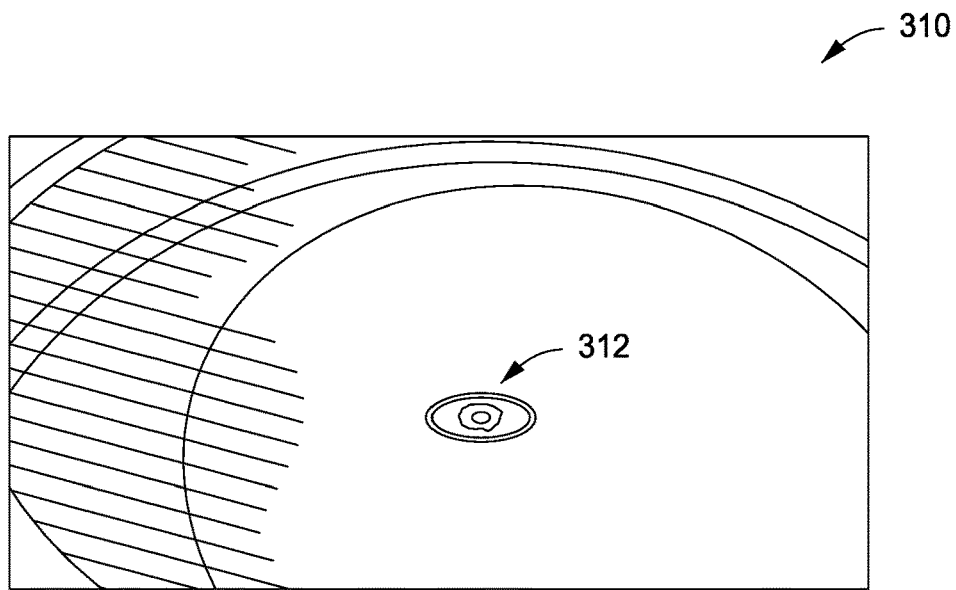
FIGS. 3A-B respectively depict light reflecting off of a portion of a process chamber surface having deposited material disposed thereon and having little or no deposited material disposed therein.
Figure 3B:
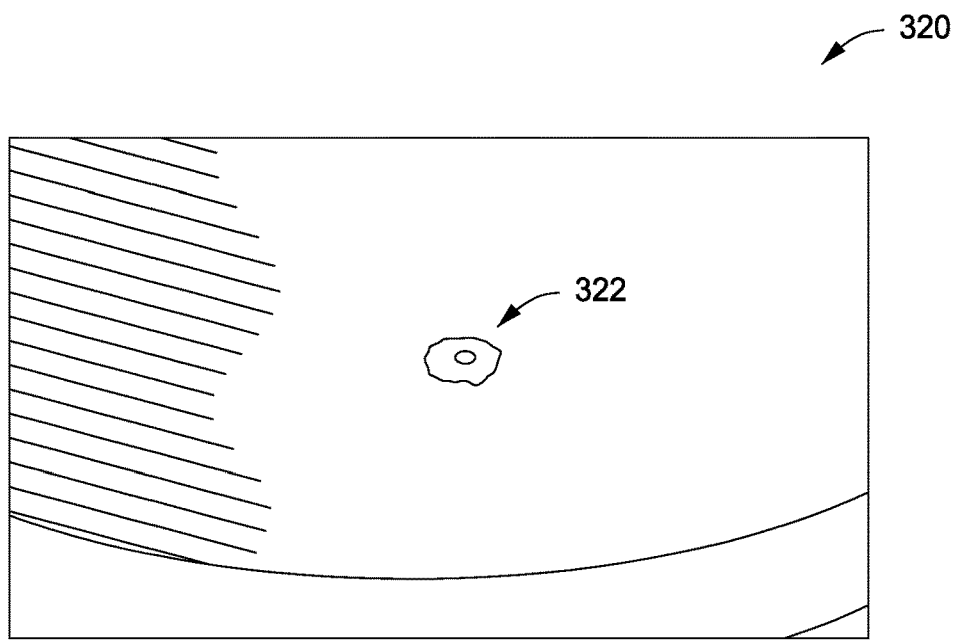

For example, FIGS. 3A-B respectively depict light reflecting off of a portion of a process chamber surface having deposited material disposed thereon and having little or no deposited material disposed therein. FIG. 3A depicts a portion 310 of a process chamber surface having materials deposited thereon. As can be seen from the Figure, a reflective pattern 312 forms when light reflects off of the process chamber surface and the deposited materials. FIG. 3B depicts a portion 320 of a process chamber surface having little or no materials deposited thereon. As can be seen from the Figure, a single specular reflection 322 forms when light reflects off of the process chamber surface without the presence of the deposited materials.

Although FIGS. 3A-B show this effect when shining light through a transparent quartz lid of a process chamber, this same effect has been observed and can be exploited with respect to chamber components formed from other materials as well. Moreover, the analysis of the detected light reflected off of the surface need not be limited to interference patterns. For example, variations in the intensity of the reflected light may also be used to determine when the deposited materials have been sufficiently removed from the process chamber surfaces.

Although described above with respect to reflections off of quartz surfaces, the above methods and apparatus may be used to determine endpoints of cleaning processes used to clean internal process chamber surfaces made of other materials as well. For example, the present methods may be used to detect endpoints for cleaning aluminum or stainless steel chamber surfaces (or any such metal surface where reflections change as a function of coverage of the surface with the deposited materials), ceramic surfaces (such as SiC, $Al_2O_3$, etc.) where the emissivity change can be captured as a function of coating thickness, gold plated surfaces where the inherent dirtiness of the shiny gold surface creates a non-specular reflection pattern (compared with specular when shiny), or the like.

While the foregoing is directed to embodiments of the present invention, other and further embodiments of the invention may be devised without departing from the basic scope thereof.

The invention claimed is:

1. A method of monitoring a process being performed in a process chamber, comprising:
    performing a cleaning process in a process chamber to remove material deposited on one or more internal surfaces of the process chamber resultant from processes performed within the process chamber, wherein the process chamber comprises a lid in an upper portion of the process chamber, the lid comprising one of the one or more internal surfaces of the process chamber;
    shining a light through the lid onto a first internal surface being cleaned;
    detecting, above the lid, the light reflected off of a material deposited on the first internal surface, wherein the light does not traverse an internal volume of the process chamber; and
    terminating the cleaning process based upon the detected reflected light.

2. The method of claim 1, wherein the light comprises ambient light shining on the first internal surface.

3. The method of claim 1, wherein detecting the light comprises:
    using a light detector comprising one or more of a photodiode or a camera to detect the light reflected off of the first internal surface.

4. The method of claim 1, wherein shining the light through the lid onto the first internal surface being cleaned further comprises:
    shining the light onto the first internal surface in a region where a higher percentage of materials are deposited as compared to other regions.

5. The method of claim 1, wherein detecting, above the lid, the light reflected off of the material deposited on the first internal surface further comprises detecting an interference pattern resultant from light reflecting off of the material deposited on the first internal surface and light reflected off a corresponding external surface of the lid.

6. The method of claim 1, wherein detecting, above the lid, the light comprises detecting an intensity of the light reflecting off of the material deposited on the first internal surface, or an intensity of the light reflecting off of the material deposited on the first internal surface and of light reflected off a corresponding external surface of a component of the process chamber.

7. The method of claim 1, wherein the light is emitted from at least one of a light source that emits a single wavelength of light, or from a light source that emits a plurality of wavelengths of light.

8. The method of claim 1, further comprising:
    shining light from a plurality of light sources; and
    measuring a thickness of a coating of the material deposited on the internal surface.

9. The method of claim 1, wherein the lid is made from quartz.

10. The method of claim 9, wherein the light is emitted from a light source disposed above the lid that emits light at a wavelength that passes through quartz.

11. The method of claim 10, wherein the light source comprises a laser, a light emitting diode (LED), or a lamp.

12. The method of claim 10, wherein the light source provides light to a portion of the lid to determine an endpoint of cleaning for the portion.

13. The method of claim 1, wherein the lid is dome shaped, reverse-curve shaped, or flat shaped.

* * * * *